US00PP13187P2

(12) United States Plant Patent
Utecht

(10) Patent No.: US PP13,187 P2
(45) Date of Patent: Nov. 5, 2002

(54) GERANIUM PLANT NAMED 'FISDIDIN'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/989,116

(22) Filed: Nov. 21, 2001

(65) Prior Publication Data

US 2002/0088035 P1 Jul. 4, 2002

(51) Int. Cl.[7] ..... A01H 5/00

(52) U.S. Cl. ..... Plt./329
(58) Field of Search ..... Plt./329

*Primary Examiner*—Kent L. Bell
(74) *Attorney, Agent, or Firm*—Foley & Lardner

(57) ABSTRACT

A new and distinct cultivar of geranium plant named 'Fisdidin', as described and illustrated, and particularly characterized by the combined features of brilliant, red-purple flowers with dark-red markings, compact to medium sized inflorescence, borne well above the foliage, medium-green leaves with slight zonation, compact to medium sized, well-branched plant habit, and mid season flowering response.

1 Drawing Sheet

BOTANICAL CLASSIFICATION

*Pelargonium zonale.*

VARIETY DENOMINATION

'Fisdidin'.

BACKGROUND OF THE INVENTION

The present invention comprises a new and distinct cultivar of geranium, botanically known as *Pelargonium zonale*, and hereinafter referred to by the cultivar name 'Fisdidin'.

'Fisdidin' is a product of a planned breeding program which had the objective of creating new geranium varieties with purple flower color, medium green foliage and relatively compact plant habit.

'Fisdidin' originated from a hybridization made by the inventor, Angelika Utecht in a controlled breeding program in Galdar, Gran Canaria, Spain, in 1996. The female parent was the patented cultivar 'Fisdino' (U.S. Plant Pat. No. 8,761), having red-purple flowers with red markings, large inflorescences, medium-green zoned foliage, and fairly vigorous growth.

The male parent of 'Fisdidin' was an unpatented hybrid seedling, no. K93-998-9, which was characterized by dark-pink flowers with white eyes at the bases of upper petals, with medium-green, zoned foliage, and compact plant habit.

'Fisdidin' was selected as one flowering plant within the progeny of the stated cross by Angelika Utecht in 1997 in a controlled environment in Galdar, Gran Canaria, Spain. The first act of asexual reproduction of 'Fisdidin' was accomplished when vegetative cuttings were taken from the initial selection in the fall of 1997 in a controlled environment in Galdar, Gran Canaria, Spain, by, or under the supervision of, Angelika Utecht.

Horticultural examination of plants grown from cuttings of the plant initiated in May 1998, in Hillscheid, Federal Republic of Germany, and continuing thereafter, has demonstrated that the combination of characteristics as herein disclosed for 'Fisdidin' are firmly fixed, reproduce true to type and are retained through successive generations of asexual reproduction.

'Fisdidin' has not been observed under all possible environmental conditions. The phenotype may vary significantly with variations in environment such as temperature, light intensity and day length. The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fisdidin' in combination distinguish this geranium as a new and distinct cultivar:

1. Intense red-purple flower color;
2. Small to medium-sized, semi-double flowers;
3. Relatively compact, semi-spherically shaped umbels well above the foliage;
4. Medium-green foliage with weak zonation;
5. Compact to medium sized, and well-branched plant habit;
6. Medium (mid season) spring flowering response.

Of the many commercial cutlivars known to the present inventor, the most similar in comparison to 'Fisdidin' is the parental variety 'Fisdino' and the related cultivar 'Fisom' (U.S. Plant Pat. No. 12,363).

In comparison to 'Fisdino', 'Fisdidin' has a similar flower color and similar markings on petals, but flowers are smaller and more round in shape. Furthermore, it is distinctly more compact and has better branching characteristics, which results in a smaller and more evenly shaped plant habit.

In comparison to 'Fisom', 'Fisdidin' has slightly more intense and more reddish colored flowers, with less distinct markings and without white base, and its inflorescence are smaller. Pedicels of 'Fisdidin' develop a somewhat stronger reddish coloring, and plant habit is more compact.

In comparison to the related cultivar 'Fisbluda' (U.S. Plant patent application Ser. No. 09/989,119), 'Fisdidin' has a less rose-red, more bluish, general hue of flower color, and upper petals do not display distinct white bases, which 'Fisbluda' possesses.

BRIEF DESCRIPTION OF THE DRAWINGS

The accompanying photographic drawing shows typical flower and foliage characteristics of 'Fisdidin' with colors being as true as possible with an illustration of this type. The drawing shows a flowering pot plant, in a 14 cm container.

DETAILED BOTANICAL DESCRIPTION

The following measurements were taken in Langley, British Columbia, Canada, on Jul. 20, 2000, 15 weeks after the planting of rooted cuttings into 6 inch pots. The plants had not been pinched. In the following description color references are made to The Royal Horticultural Society Colour Chart (R.H.S.). The color values were determined indoors from plants developed in a green-house in May 2000, in Hillscheid, Germany.

Inflorescence:
- *Type.*—Umbel.
- *Shape.*—Semi-spherical.
- *Average diameter.*—97 mm.
- *Average depth.*—55 mm.
- *Peduncle length.*—210 mm.
- *Peduncle color.*—Light green, RHS 143 B, no anthocyanin.
- *Pedicel.*—Length 21 mm.
- *Pedicel color.*—Mainly brownish-red, RHS 184 A; near the base: green, RHS 144 A.
- *Number of flowers per umbel.*—About 20–25.

Corolla:
- *Average diameter.*—42.4 mm.
- *Form.*—Semi-double.
- *Shape.*—Round outline, with a gap between upper and lower petals, slightly cup-shaped.
- *Number of petals.*—9.8.
- *Number of petaloids.*—1–3.
- *Shape of petals.*—Obovate, base acute, upper end (apex) is truncate or rounded, margins are mainly entire, but may be slightly crenated at the tip of petals.
- *Size of petals.*—Upper petals: 25 mm long, 20–21 mm wide, lower petals: 20–22 mm long, 19–21 mm wide.
- *Color (general tonality from a distance of three meters).*—Intense red-purple.
- *Color of upper petals.*—Main part RHS 66 B.
- *Markings of upper petals.*—Salmon base: RHS 47 C, and deep red macule in the middle of the petal slightly more reddish than RHS 57 A.
- *Color of lower petals.*—RHS 66 A.
- *Markings of lower petals.*—Small dark-red spot between RHS 46 A and RHS 57 A.
- *Color of lower surface of petals.*—Mainly RHS 66 C to RHS 74 B.
- *Shape of petaloids.*—Irregular.
- *Color of petaloids.*—Upper surface is RHS 66 B, Lower surface is RHS 66 C.
- *Color of sepals.*—Outer surface green, RHS 143 A to RHS 143 B, brown base RHS 181 A, inner surface light green, RHS 144 B, base RHS 179 A.
- *Number of sepals.*—5.
- *Shape of sepals.*—Linear to lanceolate, acute tip, truncate base, surface with moderate pubescence, margin entire.
- *Size of sepals.*—10–11 mm long, 5 mm wide for the largest upper sepal, 2–3 mm in width for the other sepals.

Bud: (just before petals unfold):
- *Shape.*—Elliptical.
- *Color (sepals).*—Green, RHS 143 A.
- *Color (petals).*—Bluish red, RHS 57 B to RHS 57 C.
- *Length.*—16 mm.
- *Width.*—9 mm.

Reproductive organs:
- *Androecium.*—3–5 fertile anthers, filaments white, RHS 155 A, moderate pollen, orange, RHS 30 A.
- *Gynoecium.*—One pistil, style and stigma red-purple RHS 57 A, 5 to 6-lobed stigma.
- *Fertility/seed set.*—Occasionally a few seeds develop, mainly in late summer to fall. Fruit: oblong, about 6 mm in diameter, with rostrum (beak), total length about 38 mm long. Seed: Oblong, 4–5 mm long, brown, RHS 177 B.

Spring flowering response period: In Hillscheid, Germany, in 2000, plants had on average 0.9 flowers opened 8 weeks after planting of rooted cuttings.

Outdoor flower production: Continuously flowering, the flower count in 2000 in Hillscheid, Germany, indicated about 2.3 inflorescences per plant in mid May.

Durability: Good stability of flower color, somewhat susceptible to being scorched by sun, relatively good rain resistance.

Lastingness of the individual flower: About 9 days at 18° C., about 18 days for the umbel.

Pest/disease resistance/susceptibility: No observations to date.

Fragrance: None.

PLANT

Foliage:
- *Shape.*—Kidney-shaped, cordate and open to wide open base, and with relatively distinct lobes for a zonal variety.
- *Margin.*—Bicrenated.
- *Texture.*—Upper surface smooth, velvety.
- *Size of leaf.*—85 mm wide, 51 mm long.
- *Color of upper surface.*—Medium green, approximately RHS 137 B to RHS 137 C.
- *Color of lower surface.*—Light green, RHS 137 D.
- *Color of zonation.*—Brown, about RHS 166 A, distinctness weak, about "3" in a range from 1 being not visible to 9 being very strong.
- *Petioles.*—45–55 mm long, diameter 3 mm, light green, approximately RHS 137 D.

General appearance and form:
- *Stem color.*—Green, RHS 143 B.
- *Internode length.*—About 5 mm.
- *Branching pattern.*—Average 8.8 branches.
- *Size of plants.*—Height of foliage canopy: 24.6 cm, width: 45.6 cm, measured from the top of the soil (or base of the main stem) to the foliage surface, without inflorescences.

I claim:

1. A new and distinct cultivar of geranium plant named 'Fisdidin', as described and illustrated herein.

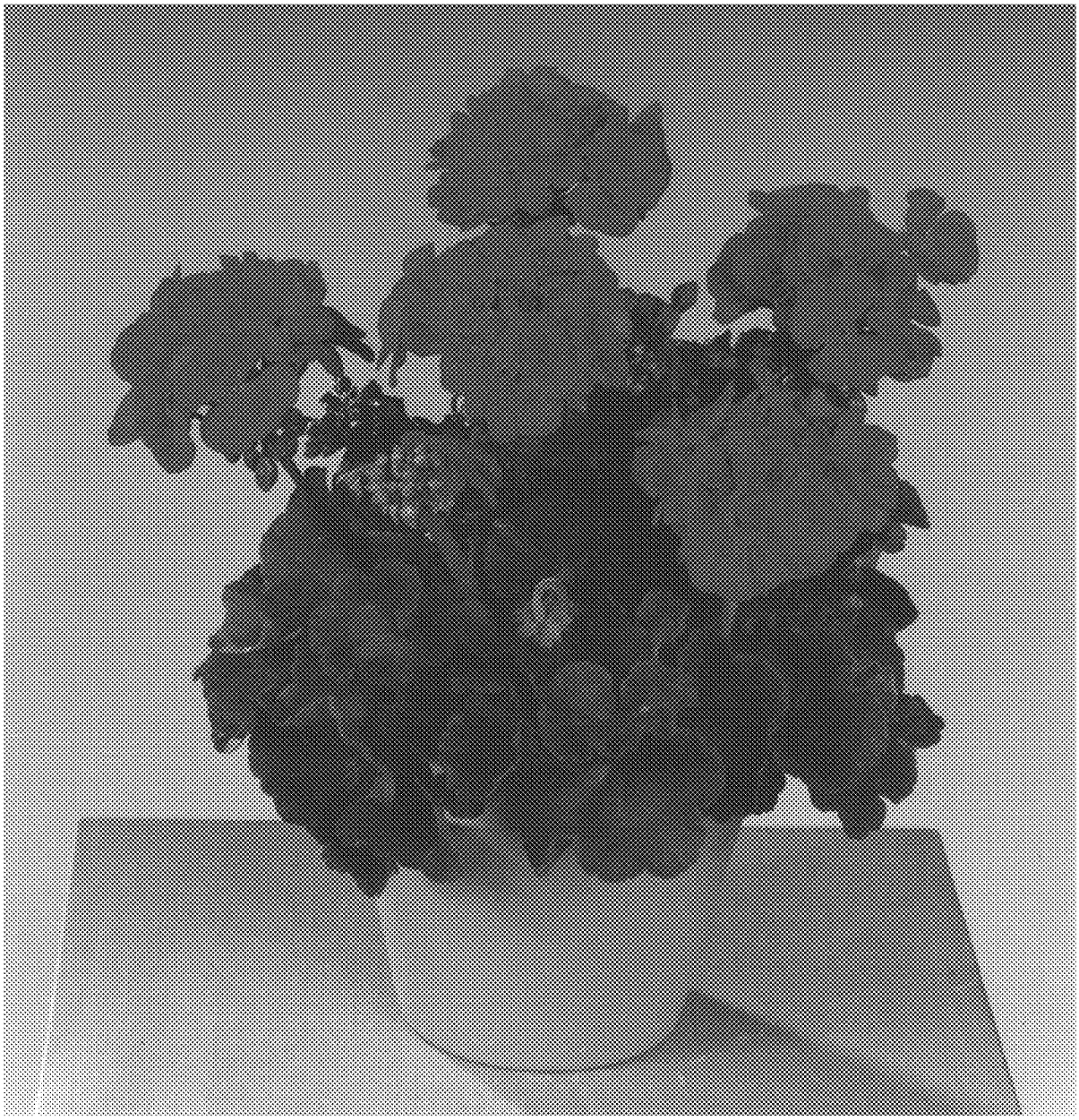

* * * * *